United States Patent
Lee et al.

(10) Patent No.: US 10,702,641 B2
(45) Date of Patent: Jul. 7, 2020

(54) VENTRICULAR ASSIST DEVICES HAVING A HOLLOW ROTOR AND METHODS OF USE

(71) Applicant: TC1 LLC, St. Paul, MN (US)

(72) Inventors: Eric T. Lee, Oakland, CA (US); William V. Hodges, Tracy, CA (US); Yi-Ren Woo, Livermore, CA (US)

(73) Assignee: TC1 LLC, St. Paul, MN (US)

( * ) Notice: Subject to any disclaimer, the term of this patent is extended or adjusted under 35 U.S.C. 154(b) by 58 days.

(21) Appl. No.: 15/196,436

(22) Filed: Jun. 29, 2016

(65) Prior Publication Data

US 2016/0375187 A1 Dec. 29, 2016

Related U.S. Application Data

(60) Provisional application No. 62/186,202, filed on Jun. 29, 2015.

(51) Int. Cl.

| *F04D 3/00* | (2006.01) |
| *A61M 1/10* | (2006.01) |
| *A61M 1/12* | (2006.01) |

(52) U.S. Cl.
CPC ........ *A61M 1/1012* (2014.02); *A61M 1/1036* (2014.02); *A61M 1/127* (2013.01); *A61M 1/101* (2013.01); *A61M 1/1013* (2014.02); *A61M 1/1015* (2014.02); *A61M 1/1017* (2014.02); *A61M 1/1031* (2014.02); *A61M 1/1086* (2013.01); *A61M 1/122* (2014.02)

(58) Field of Classification Search
CPC ...... F04D 3/00; F04D 13/0606; F04D 29/041; F04D 29/048

USPC ............................................ 417/420; 415/73
See application file for complete search history.

(56) References Cited

U.S. PATENT DOCUMENTS

| 4,688,998 | A | 8/1987 | Olsen et al. |
| 5,290,227 | A | 3/1994 | Pasque |
| 5,708,346 | A | 1/1998 | Schob |
| 5,725,357 | A | 3/1998 | Nakazeki et al. |
| 5,888,242 | A | 3/1999 | Antaki et al. |
| 5,947,703 | A | 9/1999 | Akamatsu et al. |

(Continued)

FOREIGN PATENT DOCUMENTS

| EP | 0060569 A1 | 9/1982 |
| EP | 1812094 | 8/2007 |

(Continued)

*Primary Examiner* — Jon Eric C Morales
(74) *Attorney, Agent, or Firm* — Kilpatrick Townsend & Stockton LLP

(57) ABSTRACT

Blood pumps for ventricular assist devices employ a hollow rotor to impel blood through the blood pump. A blood pump includes a housing having a housing inlet, a housing outlet, and a housing blood flow channel through which the housing inlet and the housing outlet are in fluid communication. A motor stator is disposed around the housing blood flow channel and operable to generate a rotating magnetic field. A hollow rotor is disposed within the housing blood flow channel and rotated via the rotating magnetic field. The hollow rotor has a rotor circumferential wall enclosing a rotor blood flow channel. The hollow rotor has at least one rotor blade extending inwardly from the rotor circumferential wall. The at least one rotor blade is configured to impel blood through the rotor blood flow channel when the hollow rotor is rotated via the rotating magnetic field.

26 Claims, 6 Drawing Sheets

(56) References Cited

U.S. PATENT DOCUMENTS

| | | | |
|---|---|---|---|
| 6,042,347 A | 3/2000 | Scholl et al. |
| 6,053,705 A | 4/2000 | Schob et al. |
| 6,100,618 A | 8/2000 | Schoeb et al. |
| 6,120,537 A | 9/2000 | Wampler |
| 6,222,290 B1 | 4/2001 | Schöb et al. |
| 6,234,772 B1 | 5/2001 | Wampler et al. |
| 6,244,835 B1 | 6/2001 | Antaki et al. |
| 6,249,067 B1 | 6/2001 | Schob et al. |
| 6,264,635 B1 | 7/2001 | Wampler et al. |
| 6,278,251 B1 | 8/2001 | Schöb |
| 6,351,048 B1 | 2/2002 | Schob et al. |
| 6,355,998 B1 | 3/2002 | Schöb et al. |
| 6,468,041 B2 | 10/2002 | Ozaki |
| 6,527,521 B2 | 3/2003 | Noda |
| 6,575,717 B2 | 6/2003 | Ozaki et al. |
| 6,589,030 B2 | 7/2003 | Ozaki |
| 6,605,032 B2 | 8/2003 | Benkowski et al. |
| 6,626,644 B2 | 9/2003 | Ozaki |
| 6,634,224 B1 | 10/2003 | Schöb et al. |
| 6,688,861 B2 | 2/2004 | Wampler |
| 6,707,200 B2 | 3/2004 | Carroll et al. |
| 6,817,836 B2 | 11/2004 | Nose et al. |
| 6,879,074 B2 | 4/2005 | Amrhein et al. |
| 6,949,066 B2 | 9/2005 | Bearnson et al. |
| 6,991,595 B2 | 1/2006 | Burke et al. |
| 7,112,903 B1 | 9/2006 | Schob |
| 7,138,776 B1 | 11/2006 | Gauthier et al. |
| 7,150,711 B2 | 12/2006 | Nüsser et al. |
| 7,229,474 B2 | 6/2007 | Hoffmann et al. |
| 7,239,098 B2 | 7/2007 | Masino |
| 7,284,956 B2 | 10/2007 | Nose et al. |
| 7,462,019 B1 | 12/2008 | Allarie et al. |
| 7,497,116 B2 | 3/2009 | Miyakoshi et al. |
| 7,511,443 B2 | 3/2009 | Townsend et al. |
| 7,591,777 B2 | 9/2009 | LaRose et al. |
| 7,645,225 B2 | 1/2010 | Medvedev et al. |
| 7,699,588 B2 | 4/2010 | Mendler |
| 7,854,631 B2 | 12/2010 | Townsendl et al. |
| 7,861,582 B2 | 1/2011 | Miyakoshi et al. |
| 7,887,479 B2 | 2/2011 | LaRose et al. |
| 7,951,062 B2 | 5/2011 | Morello |
| 7,976,271 B2 | 7/2011 | LaRose et al. |
| 8,007,254 B2 | 8/2011 | Marquis et al. |
| 8,157,720 B2 | 4/2012 | Marseille et al. |
| 8,303,482 B2 | 11/2012 | Schima et al. |
| 8,323,174 B2 | 12/2012 | Jeevanandam et al. |
| 8,366,411 B2 | 2/2013 | Baykut et al. |
| 8,382,830 B2 | 2/2013 | Maher et al. |
| 8,449,444 B2 | 5/2013 | Poirier et al. |
| 8,506,470 B2 | 8/2013 | LaRose et al. |
| 8,506,471 B2 | 8/2013 | Bourque |
| 8,512,013 B2 | 8/2013 | Shambaugh et al. |
| 8,517,699 B2 | 8/2013 | Horvath |
| 8,556,795 B2 | 10/2013 | Bolyard et al. |
| 8,562,508 B2 | 10/2013 | Dague et al. |
| 8,597,350 B2 | 12/2013 | Rudser et al. |
| 8,657,733 B2 | 2/2014 | Ayre et al. |
| 8,764,621 B2 | 7/2014 | Badstibner et al. |
| 8,852,072 B2 | 10/2014 | White et al. |
| 8,870,739 B2 | 10/2014 | LaRose et al. |
| 8,882,477 B2 | 11/2014 | Fritz, IV et al. |
| 8,956,275 B2 | 2/2015 | Bolyard et al. |
| 9,079,043 B2 | 7/2015 | Stark et al. |
| 9,265,870 B2 | 2/2016 | Eldridge et al. |
| 2001/0009645 A1 | 7/2001 | Noda et al. |
| 2002/0150465 A1 | 10/2002 | Rosefsky |
| 2005/0071001 A1 | 3/2005 | Jarvik |
| 2008/0292478 A1 | 11/2008 | Baykut et al. |
| 2010/0130809 A1 | 5/2010 | Morello |
| 2010/0241223 A1 | 9/2010 | Lee et al. |
| 2010/0327687 A1 | 12/2010 | Iannello et al. |
| 2011/0071337 A1 | 3/2011 | Thompson et al. |
| 2011/0237863 A1 | 9/2011 | Ricci et al. |
| 2011/0313237 A1 | 12/2011 | Miyakoshi et al. |
| 2012/0226097 A1 | 9/2012 | Smith et al. |
| 2012/0245681 A1 | 9/2012 | Casas et al. |
| 2013/0119670 A1 | 5/2013 | Rosefsky |
| 2013/0127253 A1 | 5/2013 | Stark et al. |
| 2013/0209292 A1 | 8/2013 | Baykut et al. |
| 2013/0245361 A1 | 9/2013 | Wampler |
| 2013/0314047 A1 | 11/2013 | Eagle et al. |
| 2013/0331934 A1 | 12/2013 | Kabir et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0303426 A1 | 10/2014 | Kerkhoffs et al. |
| 2014/0324165 A1 | 10/2014 | Burke |
| 2014/0357937 A1 | 12/2014 | Reyes et al. |
| 2015/0051438 A1 | 2/2015 | Taskin |
| 2015/0367050 A1 | 12/2015 | Bulent et al. |
| 2016/0144089 A1 | 5/2016 | Dur et al. |

FOREIGN PATENT DOCUMENTS

| | | |
|---|---|---|
| WO | 2005032620 A1 | 4/2005 |
| WO | 2013191667 A1 | 12/2013 |
| WO | 2014098780 A1 | 6/2014 |
| WO | 2015039605 A1 | 3/2015 |
| WO | 2016086137 | 6/2016 |
| WO | 2016187057 | 11/2016 |

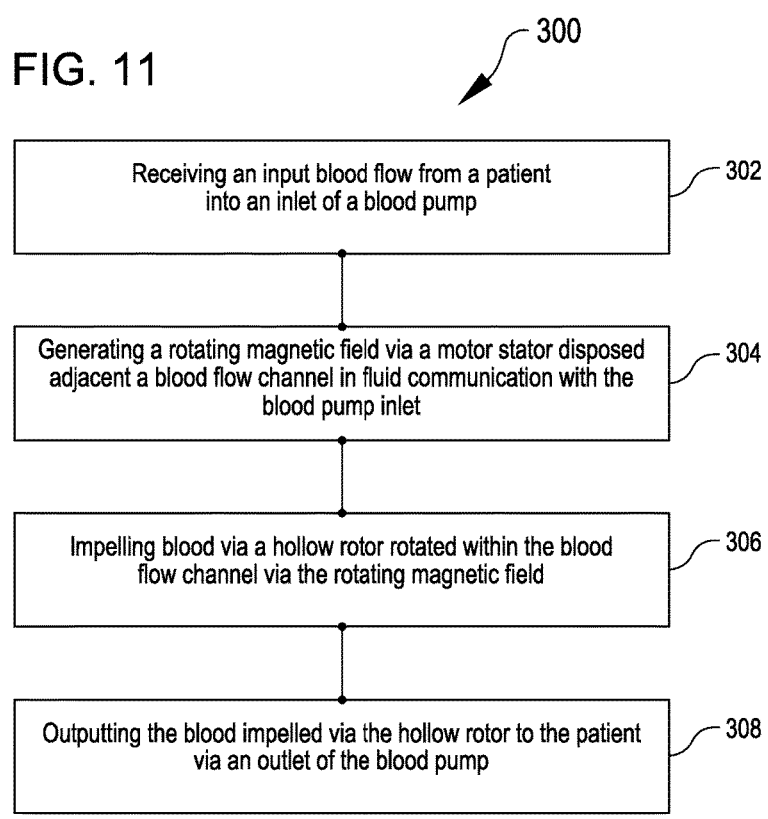

VENTRICULAR ASSIST DEVICES HAVING A HOLLOW ROTOR AND METHODS OF USE

CROSS-REFERENCES TO RELATED APPLICATIONS

This application claims the benefit of U.S. Provisional Application No. 62/186,202, filed Jun. 29, 2015, the entire contents of which are incorporated herein by reference.

BACKGROUND

This application relates generally to mechanically assisted circulation (MAC) systems, and more specifically to blood pumps that employ a hollow rotor. The use of a hollow rotor may reduce power consumption via placement of one or more drive magnets close to the outer surface of the hollow rotor thereby resulting in close coupling between the one or more drive magnets and a motor stator used to rotate the hollow rotor.

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave a heart too weak to pump enough blood to the body. As symptoms worsen, advanced heart failure develops.

A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the patient's heart's function. In view of the critical nature of the support provided by a MAC system, it is essential that power supplied to the MAC system not be interrupted for any significant period of time so as to avoid endangering the life of the patient.

VADs can be implanted in the patient's body and powered by an electrical power source inside or outside the patient's body. The power sources used can include alternating current sources such as utility provided electrical power. The use of utility provided power, however, often involves the use of a power cord, which tends to limit the travel freedom of the patient. To enable increased patient travel freedom, patient-worn batteries can be used to power a VAD for a time period limited by the power storage capacity of the batteries and the rate of power consumption by the VAD. Thus, the limits imposed on the travel freedom of the patient are based at least in part on the time period that the VAD can be operated via the patient worn batteries prior to the batteries needing to be recharged. It is therefore desirable for a VAD to have a low power consumption rate (i.e. higher power efficiency) so as to provide a longer time period before the patient-worn batteries need to be recharged.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Blood pumps for ventricular assist devices are described that employ a hollow rotor with an open central region through which blood flow is impelled via rotation of the rotor. In many embodiments, the hollow rotor includes one or more rotor blades that extend inwards from an outer circumferential wall of the rotor. By routing the blood through the hollow rotor, one or more permanent magnets can be mounted to a circumferential wall of the rotor so as to place the one or more permanent magnets in close proximity to a motor stator that generates a rotating magnetic field used to rotate the hollow rotor, thereby increasing energy efficiency of the blood pump as compared to blood pumps where the one or more permanent magnets are spaced further from the motor stator. Additionally, a blood pump that employs such a hollow rotor can have an exterior shape (e.g., substantially cylindrical) that facilitates placement of the pump within the ventricle or other suitable location within a patient.

The hollow rotor can be supported within the blood pump using any suitable approach. For example, in many embodiments, the hollow rotor is either hydrodynamically (via surface features) and/or magnetically suspended in the radial direction. The rotor can include one or more magnets disposed within a circumferential outer wall of the rotor to provide for any suitable magnetic configuration (e.g., 2-pole, 4 pole) depending upon efficiency and torque requirements. Axial alignment (and constraining axial displacement) of the hollow rotor can be achieved with passive and/or active magnets and/or hydrodynamic forces in the axial direction (parallel to the direction of blood flow through the hollow rotor).

Any suitable rotor blade design can be employed. For example, the rotor blade(s) can have a constant thickness or a tapered feature at the leading and/or trailing edge of the rotor blade. In addition, the rotor blade(s) can extend beyond the downstream end of the rotor circumferential wall to further improve the hydraulic efficiency of the blood pump.

In many embodiments, the hollow rotor is configured to minimize occurrence of thrombosis. For example, to facilitate washing, the external surface of the hollow rotor can contain open grooves connecting the inlet and the outlet ends of the rotor, and/or the rotor inlet profile can be designed to preferentially encourage flow to go into the region between the rotor and the housing fluid channel surface adjacent to the motor stator.

Although a static inlet and/or outlet stator(s) can be used, a hollow rotor can be employed in a blood pump that does not include an inlet and/or outlet stator(s). For example, a blood pump employing a hollow rotor and not including an inlet and/or outlet stator(s) can output blood from the rotor to an aft housing having a non-axisymmetric configuration where the rotational energy in the blood flow output by the rotating hollow rotor is captured and effectively converted to pressure before the blood flow exits the pump. Depending upon the efficiencies achieved and flow and pressure performance, a hollow rotor blood pump without an inlet and/or outlet stator(s) can be relatively small (e.g., length and/or outside diameter) so as to be useful for either full- or partial-support applications.

Thus, in one aspect, a blood pump of a ventricular assist device is described. The blood pump includes a housing, a motor stator, and a hollow rotor. The housing has a housing inlet, a housing outlet, and a housing blood flow channel through which the housing inlet and the housing outlet are in fluid communication. The motor stator is disposed around the housing blood flow channel and operable to generate a rotating magnetic field. The hollow rotor is disposed within the housing blood flow channel and rotated via the rotating magnetic field. The hollow rotor has a rotor inlet, a rotor outlet, and a rotor circumferential wall extending between the rotor inlet and the rotor outlet and enclosing a rotor blood flow channel through which the rotor inlet and the rotor outlet are in fluid communication. The hollow rotor has at least one rotor blade extending inwardly from the rotor circumferential wall. The at least one rotor blade is configured to impel blood through the rotor blood flow channel when the rotor is rotated via the rotating magnetic field.

In many embodiments, the blood pump includes at least one permanent magnet coupled with the hollow rotor. The at least one permanent magnet is configured to interact with the rotating magnetic field so as to rotate the hollow rotor within the housing blood flow channel. The rotor circumferential wall is configured to accommodate and support the at least one permanent magnet between the rotor blood flow channel and an inner surface of the housing blood flow channel. The blood pump can include a plurality of permanent magnets coupled with the hollow rotor. The plurality of permanent magnets can be configured to interact with the rotating magnetic field so as to rotate the hollow rotor within the housing blood flow channel. The rotor circumferential wall can be configured to accommodate and support the plurality of permanent magnets in a circumferential array between the rotor blood flow channel and an inner surface of the housing blood flow channel.

The hollow rotor can be supported using any suitable approach, including via magnetic levitation, one or more hydrodynamic bearings, and/or one or more mechanical bearings. For example, axial thrust applied to the hollow rotor by blood impelled by the hollow rotor can be reacted passively via magnetic attraction between the motor stator and the at least one permanent magnet mounted to the hollow rotor. The motor stator can be configured to levitate and rotate the hollow rotor via a combination of controlled magnetic fields and passive magnetic attraction. For example, the motor stator can include a plurality of pole pieces magnetically coupled to a common back piece, a plurality of drive coils for generating the rotating magnetic field, and a plurality of levitation coils to generate magnetic fields to levitate the hollow rotor. Each of the plurality of pole pieces can pass through one of the plurality of drive coils and one of the plurality of levitation coils. For example, each of the plurality of drive coils can be wrapped around a single one of the plurality of pole pieces and each of the plurality of levitation coils can be wrapped around an adjacent two of the plurality of pole pieces. In many embodiments, an inner surface of the housing blood flow channel and an outer surface of the rotor circumferential wall form a hydrodynamic bearing therebetween.

In many embodiments, the one or more permanent magnets are mounted to the rotor circumferential wall to place the one or more permanent magnets in close proximity to a motor stator. For example, the blood pump can be configured such that a gap between the at least one permanent magnet and the motor stator does not exceed 0.039 inch. In many embodiments, the gap does not exceed 0.019 inch.

In many embodiments, the hollow rotor has a plurality of rotor blades extending inwardly from the rotor circumferential wall. The plurality of rotor blades is configured to impel blood through the rotor blood flow channel when the hollow rotor is rotated via the rotating magnetic field. At least one of the plurality of rotor blades can extend past the rotor circumferential wall downstream of the hollow rotor.

The hollow rotor may be configured for various flow conditions and patterns as will be understood by one of skill from the description herein. The hollow rotor and blades can be configured for axial flow, centrifugal flow, or mixed flow (i.e., a combination of axial flow and centrifugal flow). For example, the hollow rotor can be configured to output axial blood flow from the rotor blood flow channel without any significant centrifugal blood flow. The hollow rotor can be configured to output blood flow from the rotor blood flow channel that includes axial blood flow and centrifugal blood flow (i.e., mixed flow).

One will appreciate that the exemplary hollow rotor does not have blades extending radially outward and are surrounded by a shroud similar to conventional pumps. As a consequence, a different design approach may be employed. The computational flow dynamics (CFD) design may take advantage of these differences to improve overall hydraulic performance, lower the hemolysis rate, and other benefits.

The housing of the blood pump can be shaped to enhance the pumping efficiency of the hollow rotor. For example, the housing can include a central flow stator at least partially extending through the rotor blood flow channel such that an annular blood flow channel is formed between the central flow stator and the rotor circumferential wall. The hollow rotor is at least partially accommodated within the annular blood flow channel and rotated therein so as to impel blood along the annular blood flow channel.

In many embodiments, the housing blood flow channel, downstream of the hollow rotor, is shaped to convert at least some of total rotational flow momentum of the blood flow output by the hollow rotor into axial flow momentum. For example, an output centerline of blood flow output from the housing outlet can be offset and/or transverse to a centerline of blood flow output by the hollow rotor such that at least some of total rotational flow momentum of the blood flow output by the hollow rotor is converted into axial flow momentum for the blood output from the housing outlet. The blood pump can include one or more stationary flow stator blades configured to convert at least some of total rotational flow momentum of the blood flow output by the hollow rotor into axial flow momentum. Further details concerning the hydraulic design of the pump can be understood from U.S. Pat. No. 9,265,870; U.S. Patent Publication No. US2014/0324165 A1; U.S. Patent Publication No. US 2016/0144089 A1; International Application No. PCT/US2016/032516; and International Application No. PCT/US2015/062689; the entire contents of which are incorporated herein for all purposes.

In many embodiments, the blood pump is adapted for use as part of a ventricular assist device. For example, the blood pump inlet can be adapted to be attached to an attachment cuff coupled with a ventricle of a patient's heart. The blood pump outlet can be adapted to be attached to an output cannula attached to the patient's aorta so the blood pump is operable to pump blood from the ventricle to the aorta.

In another aspect, a method of providing supplemental blood flow to a patient is provided. The method includes receiving an input blood flow from a patient into an inlet of a blood pump, generating a rotating magnetic field via a motor stator disposed around a blood flow channel in fluid communication with the blood pump inlet, impelling blood through a hollow rotor rotated within the blood flow channel via the rotating magnetic field, and outputting the blood impelled through the hollow rotor to the patient via an outlet of the blood pump. Any suitable blood pump employing a hollow rotor, including the blood pumps described herein, can be used to perform the acts of the method.

In another aspect, a blood pump of a ventricular assist device is described. The blood pump includes a housing defining a blood conduit, a motor stator disposed around the blood conduit and operable to generate a rotating magnetic field, and a pump rotor positioned within the blood conduit. The rotor includes a wall defining a blood flow channel therethrough, at least one inwardly extending rotor blade, and a magnet disposed within the wall for interaction with the motor stator. In many embodiments of the blood pump, the wall of the rotor is substantially thinner in dimension than the diameter of the blood flow channel.

In many embodiments of the blood pump, a portion of the rotor is substantially tubular shaped. In some of such embodiments of the blood pump, the portion the rotor has a frustoconical shape.

For a fuller understanding of the nature and advantages of the present invention, reference should be made to the ensuing detailed description and accompanying drawings.

BRIEF DESCRIPTION OF THE DRAWINGS

FIG. 11 is a simplified block diagram of a method of providing supplemental blood flow to a patient, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
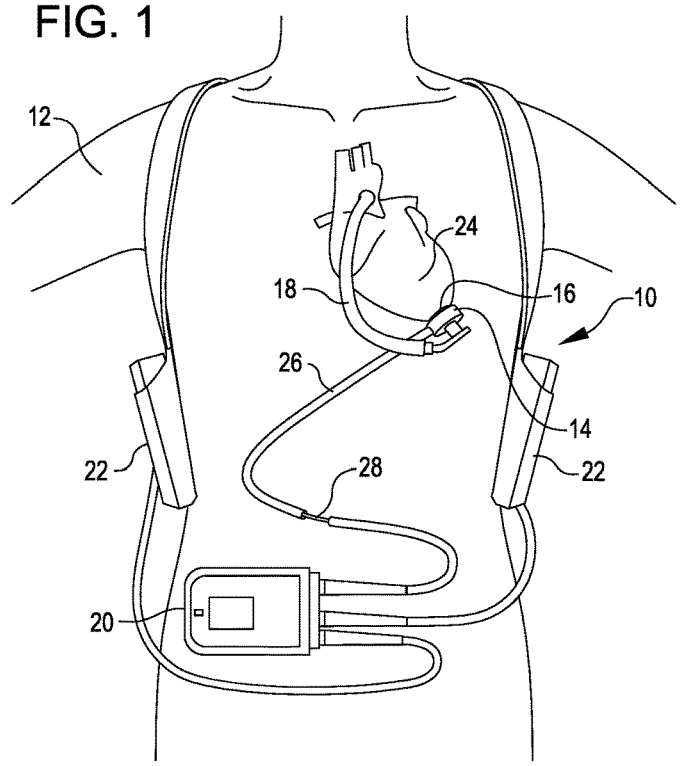
FIG. 1 is an illustration of a mechanical circulatory support system implanted in a patient's body, in accordance with many embodiments.

Referring now to the drawings, in which like reference numerals represent like parts throughout the several views, FIG. 1 shows a mechanical circulatory support system 10 implanted in a patient's body 12. The mechanical circulatory support system 10 includes an implantable blood pump assembly 14, a ventricular cuff 16, an outflow cannula 18, an external system controller 20, and power sources 22. The implantable blood pump assembly 14 can include a VAD that is attached to an apex of the left ventricle, as illustrated, or the right ventricle, or both ventricles of the heart 24. The VAD can include a blood pump that includes a hollow rotor as described in further detail herein that is capable of pumping the entire output delivered to the left ventricle from the pulmonary circulation (i.e., up to 10 liters per minute). With reference to FIG. 1, the blood pump assembly 14 can be attached to the heart 24 via the ventricular cuff 16, which can be sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline 26 that exits through the patient's abdomen 28, connects the implanted blood pump assembly 14 to the external system controller 20, which monitors system operation. Related controller systems applicable to the present invention are described in greater detail below and in U.S. Pat. Nos. 5,888,242, 6,991,595, 8,323,174, 8,449,444, 8,506,471, 8,597,350, and 8,657,733, EP 1812094, and U.S. Patent Publication Nos. 2005/0071001 and 2013/0314047, all of which are incorporated herein by reference for all purposes in their entirety. The system 10 can be powered by either one, two, or more batteries 22. It will be appreciated that although the system controller 20 and power source 22 are illustrated outside/external to the patient body, the driveline 26, system controller 20 and/or power source 22 may be partially or fully implantable within the patient, as separate components or integrated with the blood pump assembly 14. Examples of such modifications are further described in U.S. Pat. Nos. 8,562,508 and 9,079,043, all of which are incorporated herein by reference for all purposes in their entirety.

Figure 2:
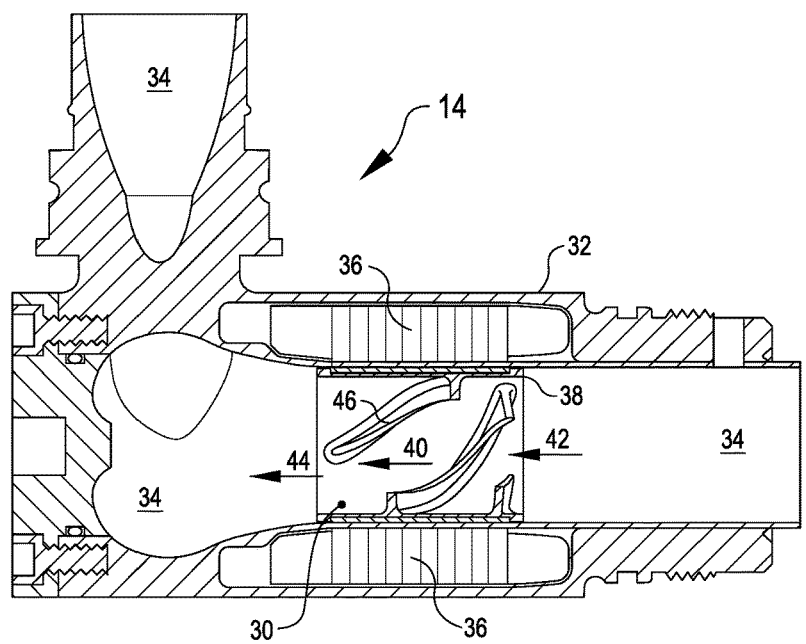
FIG. 2 is a cross-sectional view of a blood pump, in accordance with many embodiments.

FIG. 2 shows a cross-sectional view of a blood pump assembly 14 that includes a hollow rotor 30, in accordance with many embodiments. The blood pump assembly 14 is operable to pump blood via rotation of the hollow rotor 30. The blood pump assembly 14 can be adapted to employ any of the hollow rotors described herein. The blood pump assembly 14 includes a housing 32 forming a blood flow channel 34, the hollow rotor 30, and a motor stator 36 operable to generate a rotating magnetic field used to rotate the hollow rotor 30 within the blood flow channel 34. The hollow rotor 30 has a circumferential wall 38 that defines a rotor blood channel 40 through which an inlet 42 of the hollow rotor 30 is in fluid communication with an outlet 44 of the hollow rotor 30. In the embodiment shown, a plurality of rotor blades 46 extend inward from the circumferential wall 38 and have a helical shape to impel blood through the hollow rotor 30 during rotation of the hollow rotor 30 within the blood flow channel 34.

Figure 8:
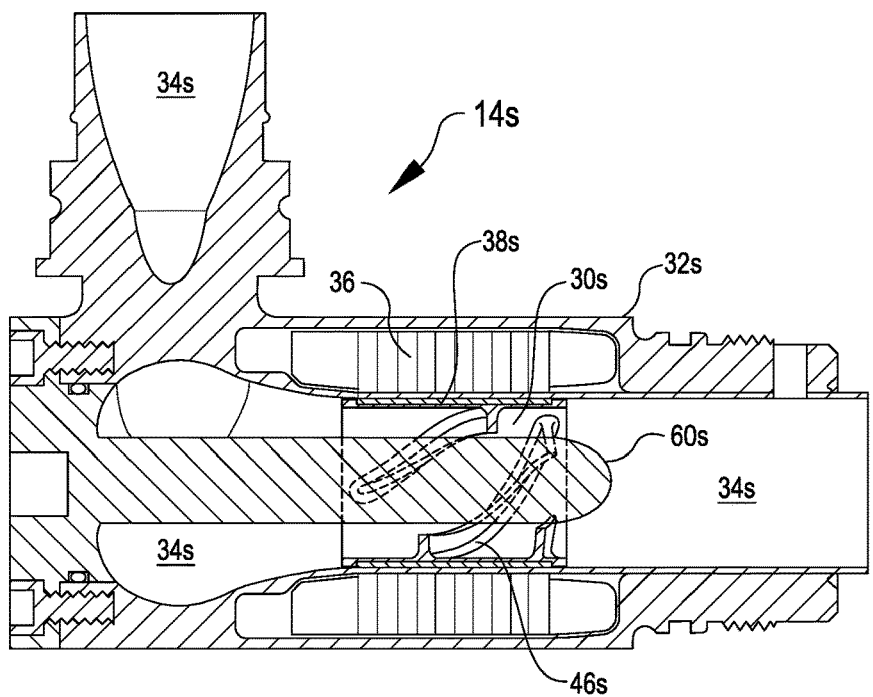
FIG. 8 is a cross-sectional view of a blood pump having a central flow stator, in accordance with many embodiments.

As shown in FIG. 2 and FIG. 8, the blood pump assembly 14, 14s includes the motor stator 36. The motor stator 36 is disposed within a recess of the housing 32 and is sealed from the blood flow channel 34 and an external environment. The motor stator 36 generates a magnetic field to drive a magnetic material embedded inside the circumferential wall of the hollow rotor to rotate and result in the action of pumping blood. Suitable magnetic materials include, but are not limited to, a permanent magnet (for example, a ferromagnetic material such as iron or nickel).

Figure 3:
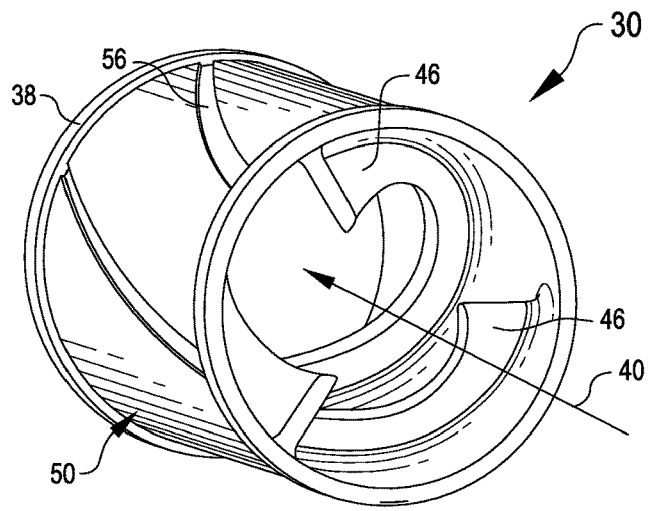
FIG. 3 is an isometric view of a hollow rotor, in accordance with many embodiments.
Figure 4:
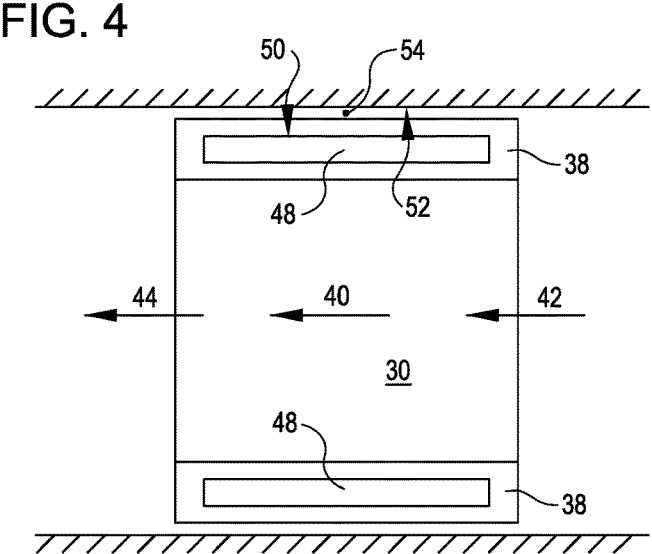
FIG. 4 is a cross-sectional illustration of a hollow rotor and interfacing housing channel, in accordance with many embodiments.

FIG. 3 is an isometric view of the hollow rotor 30 showing the helically-shaped rotor blades 46 extending inwardly into the rotor blood flow channel 40. As illustrated in FIG. 4, a permanent magnet 48 is mounted in the circumferential wall 38 of the hollow rotor 30. The permanent magnet 48 provides for magnetic coupling between the hollow rotor 30 and the rotating magnetic field generated by the motor stator 36 so as to drive rotation of the hollow rotor 30. Although the illustrated embodiment shows a single permanent magnet mounted in the circumferential wall, any suitable number of permanent magnets (e.g., 1, 2, 3, 4, or more) can be mounted in the circumferential wall 38 so as to magnetically couple with the rotating magnetic field generated by the motor stator 36. Mounting the permanent magnet 48 in the circumferential wall 38 places the permanent magnet 48 in close proximity to the motor stator 36, thereby increasing energy efficiency relative to motors in which the rotor magnet(s) is disposed further away from the motor stator 36.

In the exemplary pump of FIG. 3 and FIG. 4 the circumferential wall 38 (and magnet (48) is positioned relatively close to the motor stator 36. By moving the magnet 48 closer to the stator 36 the efficiency of the motor is significantly increased without a decrease in hydraulic efficiency. With conventional designs the efficiency is diminished by the space taken up by the blades positioned between the magnets in the centrally-located impeller hub and the surrounding motor stator.

In some embodiments, an external surface 50 of the rotor circumferential wall 38 and an interfacing internal surface 52 of the housing blood flow channel 34 are designed and configured to form a hydrodynamic bearing 54 therebetween. For example, the rotor external surface 50 and/or the interfacing internal surface 52 of the housing blood flow channel 34 can have one or more grooves 56 to facilitate distribution and movement of blood between the rotor external surface 50 and the interfacing housing internal surface 52 to provide suitable lubrication and suitable washing to prevent thrombosis during rotation of the hollow rotor 30. In one example, the rotor surface 50 and internal surface 52 are positioned close enough to each other during operation to form a thin film of fluid and build hydrodynamic pressure.

Figure 5:
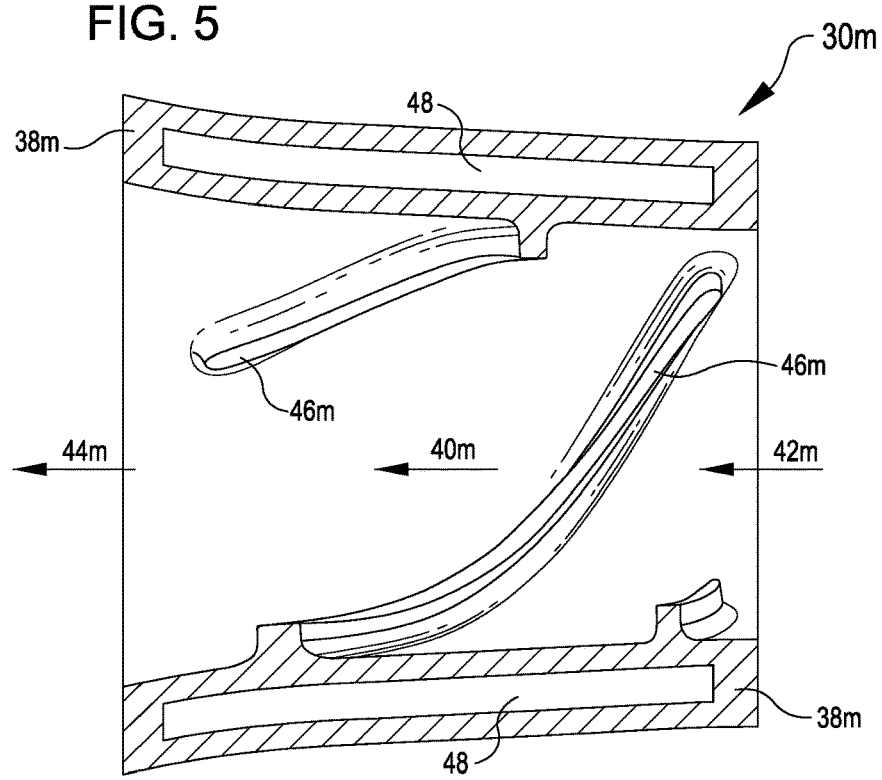
FIG. 5 is a cross-sectional view of a hollow rotor configured to output mixed flow, in accordance with many embodiments.

FIG. 5 shows a cross-section of a hollow rotor 30m, in accordance with many embodiments, that is configured to output mixed blood flow (i.e., a combination of axial blood flow and centrifugal blood flow). The hollow rotor 30m has a non-cylindrical outer wall 38m that defines a rotor blood channel 40m through which an inlet 42m of the hollow rotor 30m is in fluid communication with an outlet 44m of the hollow rotor 30m. The cross-sectional area of the rotor blood flow channel 40m increases in the direction of blood flow. This can serve to generate both centrifugal and axial components to the blood flow. The increasing diameter of the blood flow channel can also reduce losses as the fluid is accelerated out of the impeller thereby increasing hydraulic efficiency. In the embodiment shown, a plurality of rotor blades 46m extend inward from the circumferential wall 38m and have a helical shape to impel blood through the hollow rotor 30m during rotation of the hollow rotor 30m. In the embodiment shown, the hollow rotor 30m includes a permanent magnet 48m mounted in the circumferential wall 38m of the hollow rotor 30m for magnetic coupling between the hollow rotor 30m and the rotating magnetic field generated by a motor stator 36.

In various embodiments, the interfacing housing internal surface is shaped to cooperate with the frustoconical shape of the rotor 30m to create axial and/or radial hydrodynamic forces. The axial component can be configured to counteract the axial forces from the fluid. A biasing force can be applied to stabilize the rotor in the housing. For example, the stator and/or additional magnets can be provided in an axially offset position to apply an axial biasing force to the impeller magnets.

Figure 6:
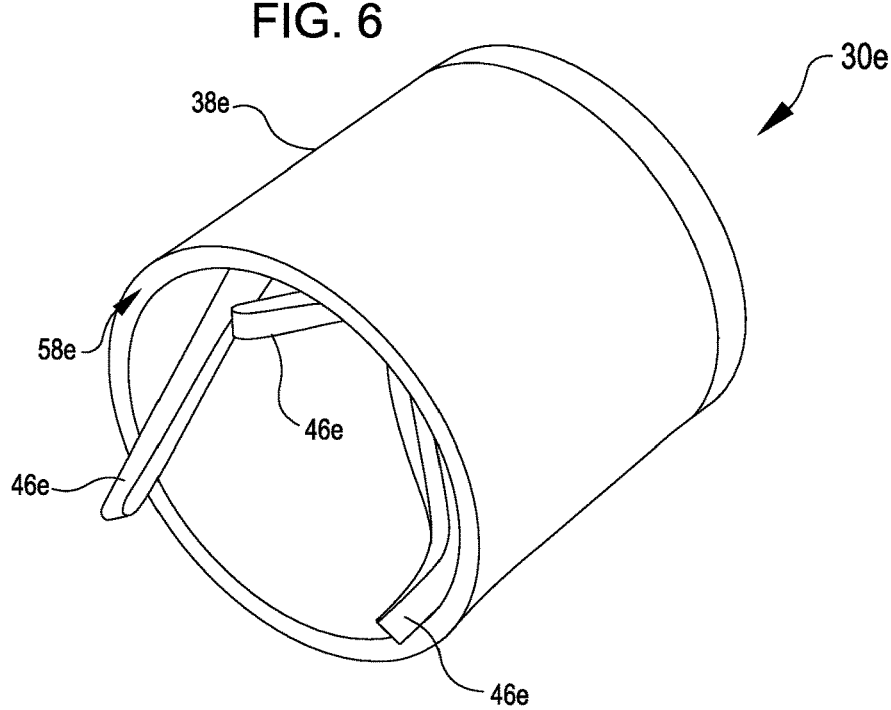
FIG. 6 is an isometric view of a hollow rotor having rotor blades that extend downstream of a circumferential wall of the hollow rotor, in accordance with many embodiments.
Figure 7:
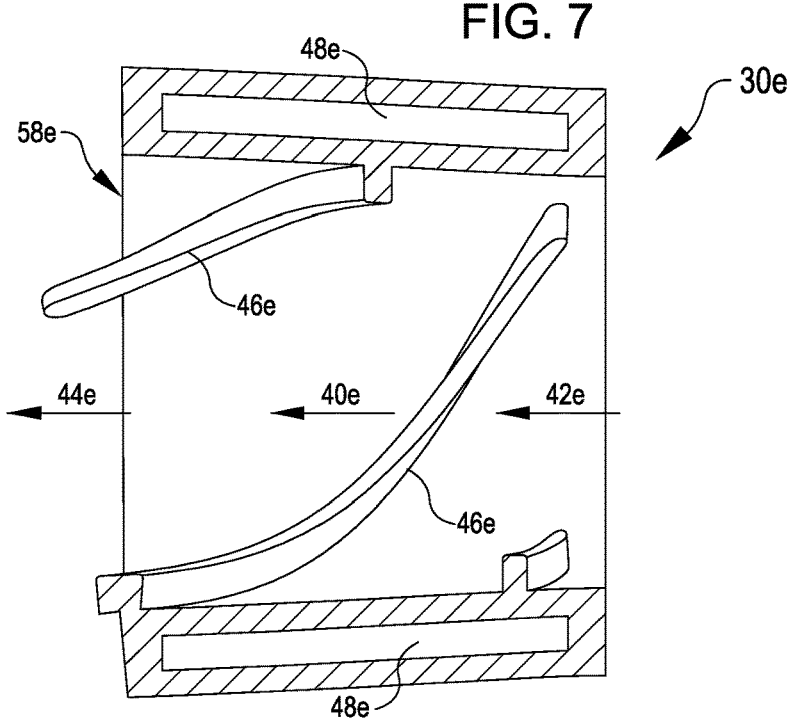
FIG. 7 is a cross-sectional view of the hollow rotor of FIG. 6.

FIG. 6 and FIG. 7 illustrate a hollow rotor 30e having rotor blades 46e that extend beyond a downstream end 58e of the rotor circumferential wall 38e. Increased pumping (hydraulic) efficiency may be obtained by extending the rotor blades 46e beyond the downstream end 58e relative to similar hollow rotors without such extended rotor blades. In the illustrated embodiment, the hollow rotor 30e has a non-cylindrical outer wall 38e that defines a rotor blood channel 40e through which an inlet 42e of the hollow rotor 30e is in fluid communication with an outlet 44e of the hollow rotor 30e. The cross-sectional area of the rotor blood flow channel 40e increases in the direction of blood flow. In the embodiment shown, a plurality of rotor blades 46e extend inward from the circumferential wall 38e and have a generally helical shape to impel blood through the hollow rotor 30e during rotation of the hollow rotor 30e. In the embodiment shown, the hollow rotor 30e includes a permanent magnet 48e is mounted in the circumferential wall 38e of the hollow rotor 30e for magnetic coupling between the hollow rotor 30e and the rotating magnetic field generated by a motor stator. While the hollow rotor 30e is illustrated has having a non-cylindrical circumferential wall 38e, rotor blades that extend beyond the down-stream edge of the circumferential wall can be employed on any of the hollow rotors described herein including the hollow rotor 30, which can have a cylindrical outer surface.

FIG. 8 is a cross-sectional view of a blood pump 14s having a hollow rotor 30s and a central flow stator 60s, in accordance with many embodiments. The blood pump 14s is configured similar to the blood pump 14 but further includes the central flow stator 60s, which in the illustrated embodiment extends through the hollow rotor 30s. The blood pump 14s includes a housing 32s, which is similar to the housing 32 of the blood pump 14, but includes the central flow stator 60s. The housing 32s forms a blood flow channel 34s through which blood is pumped via rotation of the hollow rotor 30s. The blood flow channel 34s and the central flow stator 60s combine to form an annularly shaped segment of the blood flow channel 34s in which the hollow rotor 30s is disposed and rotated via a motor stator 36. The hollow rotor 30s has rotor blades 46s that extend inward from a circumferential wall 38s to within a suitable clearance from the central flow stator 60s. The rotor blades 46s have a helical shape to impel blood through the hollow rotor 30e during rotation of the hollow rotor 30e. The central flow stator 60s contributes to the pumping efficiency of the blood pump 14s by reducing tip losses at the inner tips of the rotor blades 46s.

One will appreciate that the exemplary hollow rotors 30, 30m, 30e, 30s do not have blades extending radially outward and are surrounded by a shroud similar to conventional pumps. As a consequence, a different design approach may be employed. For example, computational flow dynamics (CFD) can be used to take advantage of these differences to improve overall hydraulic performance, lower the hemolysis rate, and other benefits.

Figure 9:
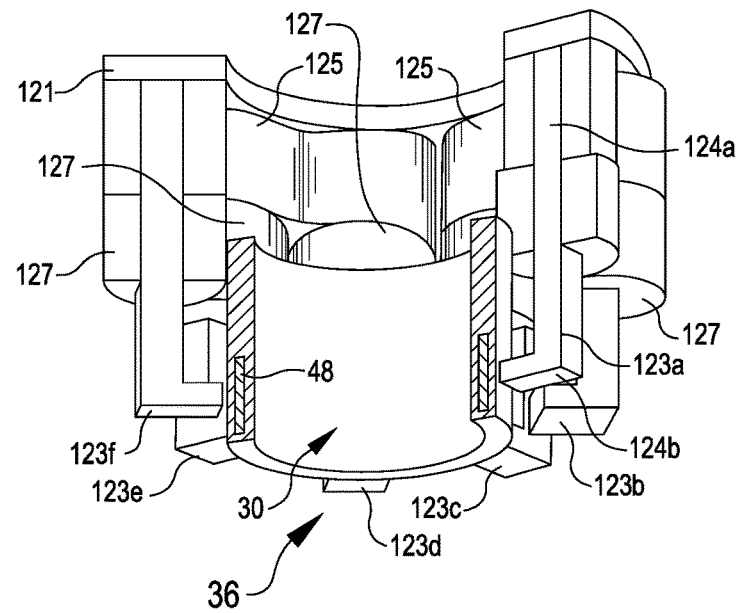
FIG. 9 is a partial cut-away isometric view of a motor stator of a blood pump, in accordance with many embodiments.

Any suitable motor stator can be employed to rotate the hollow rotors described herein. For example, referring now to FIG. 9, an additional embodiment of the motor stator 36 utilizing a magnetic levitation bearing will now be described. In the illustrated additional embodiment, the motor stator 36 includes a back iron 121 and pole pieces 123a-123f arranged at intervals. The back iron 121 extends around the blood flow channel 34, 34s and is formed as a generally flat disc of a ferromagnetic material, such as steel, in order to conduct magnetic flux. The back iron 121 provides a base for the pole pieces 123a-123f.

Each of the pole piece 123a-123f is L-shaped and has a drive coil 125 for generating an electromagnetic field to rotate the hollow rotor 30, 30m, 30e, 30s. For example, the pole piece 123a has a first leg 124a that contacts the back iron 121 and extends from the back iron 121. The pole piece 123a may also have a second leg 124b that extends from the first leg 124a towards the permanent magnet 48 mounted in the hollow rotor 30, 30m, 30e, 30s.

The implantable blood pump 14, 14s can include one or more Hall sensors that may provide an output voltage that is directly proportional to a strength of a magnetic field that is located in between at least one of the pole pieces 123a-123f and the permanent magnet 48. The output voltage(s) can provide feedback to control electronics of the blood pump 14, 14s to determine if the hollow rotor 30, 30m, 30e, 30s and/or the permanent magnet 48 is not at its intended position for the operation of the blood pump 14, 14s. For example, a position of the hollow rotor 30, 30m, 30e, 30s and/or the permanent magnet 48 can be adjusted, e.g., the hollow rotor 30, 30m, 30e, 30s or the permanent magnet 48 may be pushed or pulled towards a center of the blood flow channel 34, 34s or towards a center of the motor stator 36. In many embodiments, the implantable blood pump 14, 14s includes the control electronics, which can be disposed in any suitable location within the blood pump 14, 14s, such as adjacent to the back iron 121.

Each of the pole pieces 123a-123f can also have a levitation coil 127 for generating an electromagnetic field to control the radial position of the hollow rotor 30, 30m, 30e, 30s. Each of the drive coils 125 and the levitation coils 127 includes multiple windings of a conductor around the pole pieces 123a-123f. Particularly, each of the drive coils 125 can be wound around two adjacent ones of the pole pieces 123, such as pole pieces 123d and 123e, and each levitation coil 127 can be wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the motor stator 36 can be arranged in opposing pairs and controlled to drive the rotor and to radially levitate the hollow rotor 30, 30m, 30e, 30s by generating electromagnetic fields that interact with the permanent magnetic poles S and N of the permanent magnet 48. Because the motor stator 36 includes both the drive coils 125 and the levitation coils 127, only a single stator is needed to levitate the hollow rotor 30, 30m, 30e, 30s using only passive and active magnetic forces. The permanent magnet 48 in this configuration has only one magnetic moment and can be formed from a monolithic permanent magnetic body 48. For example, the motor stator 36 can be controlled as discussed in U.S. Pat. No. 6,351,048, the entire contents of which are incorporated herein by reference for all purposes. The control electronics and the motor stator 36 receive electrical power from a remote power supply via the drive line 26 (FIG. 1). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, are hereby incorporated by reference for all purposes in their entirety.

The hollow rotor 30, 30m, 30e, 30s is arranged within the blood flow channel 34, 34s such that the permanent magnet 48 is proximate the second legs 124b of the pole pieces 123. Interaction between the permanent magnet 48 and ferromagnetic material of the pole pieces 123 provides a passive axial centering force that resists movement of the hollow rotor axially along the blood flow channel.

The hollow rotor 30, 30m, 30e, 30s can be radially suspended by active control of the levitation coils 127 as discussed above. Because the hollow rotor can be axially suspended by passive interaction of the permanent magnet 48 and the motor stator 120, the axial position of the hollow rotor along the blood flow channel 34, 34s can be controlled without the use of active levitation components.

In use, the drive coils 125 of the motor stator 36 generate electromagnetic fields through the pole pieces 123 that selectively attract and repel the magnetic north pole N and the magnetic south pole S of the permanent magnet 48 to cause the hollow rotor 30, 30m, 30e, 30s to rotate within motor stator 36. For example, the one or more Hall sensors can be used to sense a current position of the hollow rotor and/or the permanent magnet 48, wherein the output voltage of the one or more Hall sensors can be used to control the motor stator 36 to selectively attract and repel the magnetic north pole N and the magnetic south pole S of the permanent magnet 48 to cause the hollow rotor to rotate within motor stator 36. As the hollow rotor rotates, the rotor blades 46, 46m, 46e, 46s force blood through the hollow rotor such that blood is forced out of the blood pump 14, 14s into the output flow cannula 18 (FIG. 1).

Figure 10:
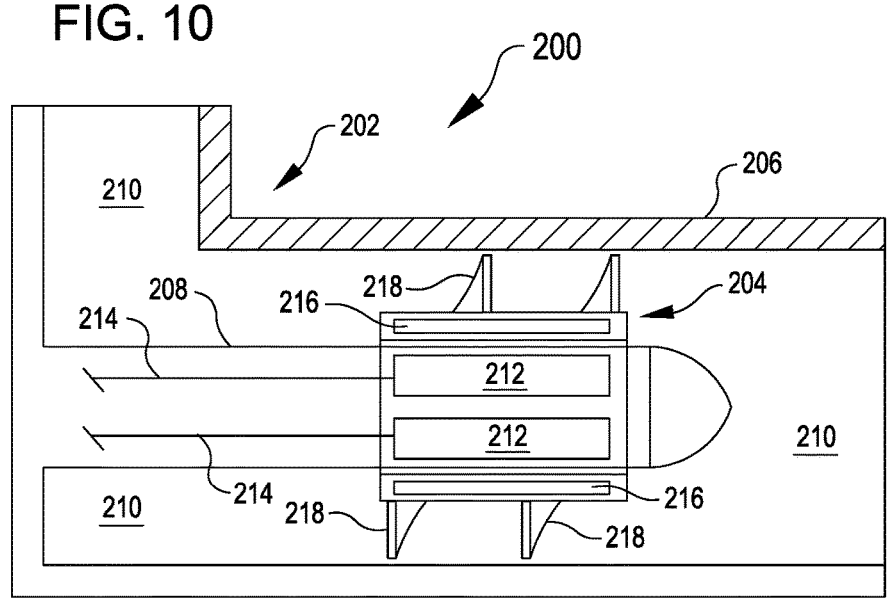
FIG. 10 schematically illustrates an alternate embodiment of a blood pump having a hollow rotor, in accordance with many embodiments.

FIG. 10 schematically illustrates an implantable blood pump 200, in accordance with many embodiments. The blood pump 200 includes a subassembly 202 and a hollow rotor 204. The subassembly 202 includes a housing 206 having an elongated motor stator support member 208 and forming a blood flow channel 210. The subassembly 202 further includes a motor stator 212 mounted in the support member 208. The motor stator 212 is operable to generate a rotating magnetic field extending into the annular segment of the blood flow channel 210 surrounding the support member 208 via controlled application of drive current via stator coils leads 214. The hollow rotor 204 includes one or more permanent magnets 216 mounted in an inner circumferential wall of the hollow rotor 204. The rotating magnetic field generated by the motor stator 212 interacts with the one or more permanent magnets 216 to rotate the hollow rotor 204 around the support member 208. The hollow rotor 204 has one or more rotor blades 218 extending outward from the inner circumferential wall of the hollow rotor 204 into an annular segment of the blood flow channel 210 surrounding the support member 208. Rotation of the hollow rotor 204 rotates the rotor blades 218 within the annular segment of the blood flow channel 210 thereby impelling blood through the blood pump 200 into the output flow cannula 18 (FIG. 1).

Operation and control of the motor stator 212 can be accomplished using approaches corresponding to those described herein with regard to the motor stator 36. For example, the motor stator 212 can include drive and levitation coils to rotate the hollow rotor 204, controllably levitate the hollow rotor radially relative to the blood flow direction, and control the position of the hollow rotor parallel to the blood flow direction via passive magnetic attraction as described herein with respect to the motor stator 36 and the permanent magnet 48 of the hollow rotor 30, 30m, 30e, 30s.

Additionally, the inner surface of the inner circumferential wall of the hollow rotor 204 and the corresponding interfacing external surface of the support member 208 can be configured with surface features (e.g., grooves configured to produce blood flow and/or distribution) to form a hydrodynamic bearing disposed therebetween.

FIG. 11 is a simplified block diagram of a method 300 of providing supplemental blood flow to a patient, in accordance with many embodiments. Any suitable implantable blood pump having a hollow rotor, including any of the implantable blood pumps described herein can be used to accomplish the acts of the method 300. The method 300 includes receiving an input blood flow from a patient into an inlet of a blood pump (act 302). A rotating magnetic field is generated via a motor stator disposed adjacent a blood flow channel in fluid communication with the blood pump inlet (act 304). Blood is impelled via a hollow rotor rotated within the blood flow channel via the rotating magnetic field (act 306). In many embodiments, the blood is impelled through the hollow rotor. The blood impelled via the hollow rotor is output to the patient via an outlet of the blood pump (act 308).

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A blood pump of a ventricular assist device, the blood pump comprising:
a housing having a housing inlet, a housing outlet, and a housing blood flow channel through which the housing inlet and the housing outlet are in fluid communication, the housing comprising a central flow stator;
a motor stator disposed around the housing blood flow channel and operable to generate a rotating magnetic field; and
a hollow rotor disposed within the housing blood flow channel and rotated via the rotating magnetic field; the hollow rotor having a rotor inlet, a rotor outlet, and a rotor circumferential wall extending between the rotor inlet and the rotor outlet and enclosing a rotor blood flow channel through which the rotor inlet and the rotor outlet are in fluid communication; the hollow rotor having at least one rotor blade extending inwardly from the rotor circumferential wall, the at least one rotor blade being configured to impel blood through the rotor blood flow channel when the hollow rotor is rotated via the rotating magnetic field, the central flow stator at least partially extending through the rotor blood flow channel such that an annular blood flow channel is formed between the central flow stator and the rotor circumferential wall, the hollow rotor being accommodated within the annular blood flow channel and rotated therein so as to impel blood along the annular blood flow channel.

2. The blood pump of claim 1, comprising at least one permanent magnet coupled with the hollow rotor and configured to interact with the rotating magnetic field so as to rotate the hollow rotor within the housing blood flow channel, the rotor circumferential wall being configured to accommodate and support the at least one permanent magnet between the rotor blood flow channel and an inner surface of the housing blood flow channel.

3. The blood pump of claim 1, comprising a plurality of permanent magnets coupled with the hollow rotor and configured to interact with the rotating magnetic field so as to rotate the hollow rotor within the housing blood flow channel, the rotor circumferential wall being configured to accommodate and support the plurality of permanent magnets in a circumferential array between the rotor blood flow channel and an inner surface of the housing blood flow channel.

4. The blood pump of claim 2, wherein axial thrust applied to the hollow rotor by blood impelled by the hollow rotor is reacted passively via magnetic attraction between the at least one permanent magnet and the motor stator.

5. The blood pump of claim 2, wherein motor stator is configured to levitate and rotate the hollow rotor via a combination of controlled magnetic fields and passive magnetic attraction.

6. The blood pump of claim 2, wherein the motor stator comprises a plurality of pole pieces magnetically coupled to a common back piece, a plurality of drive coils for generating the rotating magnetic field, and a plurality of levitation coils to generate magnetic fields to levitate the hollow rotor; each of the plurality of pole pieces passing through one of the plurality of drive coils and one of the plurality of levitation coils.

7. The blood pump of claim 6, wherein each of the plurality of drive coils is wrapped around a single one of the plurality of pole pieces and each of the plurality of levitation coils is wrapped around an adjacent two of the plurality of pole pieces.

8. The blood pump of claim 2, wherein a gap between the at least one permanent magnet and the motor stator does not exceed 0.039 inch.

9. The blood pump of claim 8, wherein the gap does not exceed 0.019 inch.

10. The blood pump of claim 1, wherein an inner surface of the housing blood flow channel and an outer surface of the rotor circumferential wall form a hydrodynamic bearing therebetween.

11. The blood pump of claim 1, wherein the hollow rotor has a plurality of rotor blades extending inwardly from the rotor circumferential wall, the plurality of rotor blades being configured to impel blood through the rotor blood flow channel when the hollow rotor is rotated via the rotating magnetic field.

12. The blood pump of claim 10, wherein at least one of the plurality of rotor blades extends past the rotor circumferential wall downstream of the hollow rotor.

13. The blood pump of claim 1, wherein the hollow rotor is configured to output axial blood flow from the rotor blood flow channel without any significant centrifugal blood flow.

14. The blood pump of claim 1, wherein the hollow rotor is configured to output blood flow from the rotor blood flow channel that includes axial blood flow and centrifugal blood flow.

15. The blood pump of claim 1, wherein the housing blood flow channel, downstream of the hollow rotor, is shaped to convert at least some of total rotational flow momentum of the blood flow output by the hollow rotor into axial flow momentum.

16. The blood pump of claim 15, wherein an output centerline of blood flow output from the housing outlet is offset and transverse to a centerline of blood flow output by the hollow rotor such that at least some of total rotational flow momentum of the blood flow output by the hollow rotor is converted into axial flow momentum for the blood output from the housing outlet.

17. The blood pump of claim 15, comprising one or more stationary flow stator blades configured to convert at least some of total rotational flow momentum of the blood flow output by the hollow rotor into axial flow momentum.

18. The blood pump of claim 1, wherein the blood pump inlet is adapted to be attached to an attachment cuff coupled with a ventricle of a patient's heart and the blood pump outlet is adapted to be attached to an output cannula attached to the patient's aorta so as to be operable to pump blood from the ventricle to the aorta.

19. A method of providing supplemental blood flow to a patient, the method comprising:
receiving an input blood flow from a patient into an inlet of a blood pump;
generating a rotating magnetic field via a motor stator disposed around an annular blood flow channel in fluid communication with the blood pump inlet, the annular blood flow channel extending around a central flow stator;
impelling blood through the annular blood flow channel by rotating a hollow rotor via the rotating magnetic field; the hollow rotor having a rotor inlet, a rotor outlet, and a rotor circumferential wall extending between the rotor inlet and the rotor outlet and enclosing a rotor blood flow channel through which the rotor inlet and the rotor outlet are in fluid communication; the hollow rotor having at least one rotor blade extending inwardly from the rotor circumferential wall; the at least one rotor blade being configured to impel blood through the rotor blood flow channel when the hollow rotor is rotated via the rotating magnetic field, the central flow stator at least partially extending through the rotor blood flow channel; and
outputting the blood impelled through the hollow rotor to the patient via an outlet of the blood pump in fluid communication with the rotor outlet.

20. The method of claim 19, wherein the blood impelled through the hollow rotor is output from the rotor outlet without any significant centrifugal blood flow.

21. The method of claim 19, wherein the blood impelled through the hollow rotor is output from the rotor outlet with axial blood flow and centrifugal blood flow.

22. The method of claim 19, further comprising converting at least some of total rotational flow momentum of the blood flow output by the hollow rotor into axial flow momentum.

23. A blood pump of a ventricular assist device, the blood pump comprising:
a housing having a housing inlet, a housing outlet, and a housing blood flow channel through which the housing inlet and the housing outlet are in fluid communication;
a motor stator disposed around the housing blood flow channel and operable to generate a rotating magnetic field;
a hollow rotor disposed within the housing blood flow channel and rotated via the rotating magnetic field; the hollow rotor having a rotor inlet, a rotor outlet, and a rotor circumferential wall extending between the rotor inlet and the rotor outlet and enclosing a rotor blood flow channel through which the rotor inlet and the rotor outlet are in fluid communication; the hollow rotor comprising at least one rotor blade extending inwardly from the rotor circumferential wall, the at least one rotor blade being configured to impel blood through the rotor blood flow channel when the hollow rotor is rotated via the rotating magnetic field; and
at least one permanent magnet coupled with the hollow rotor and configured to interact with the rotating magnetic field so as to rotate the hollow rotor within the housing blood flow channel, the rotor circumferential wall being configured to accommodate and support the at least one permanent magnet between the rotor blood flow channel and an inner surface of the housing blood flow channel,
wherein the motor stator comprises a plurality of pole pieces magnetically coupled to a common back piece, a plurality of drive coils for generating the rotating magnetic field, and a plurality of levitation coils to generate magnetic fields to levitate the hollow rotor; each of the plurality of pole pieces passing through one of the plurality of drive coils and one of the plurality of levitation coils, and
wherein each of the plurality of drive coils is wrapped around a single one of the plurality of pole pieces and each of the plurality of levitation coils is wrapped around an adjacent two of the plurality of pole pieces.

24. The blood pump of claim 23, wherein a portion the hollow rotor is substantially tubular shaped.

25. The blood pump of claim 24, wherein the portion the hollow rotor has a frustoconical shape.

26. The blood pump of claim 23, wherein the wall of the hollow rotor is substantially thinner in dimension than the diameter of the housing blood flow channel.

* * * * *